US008273911B2

(12) United States Patent
Mignani et al.

(10) Patent No.: US 8,273,911 B2
(45) Date of Patent: *Sep. 25, 2012

(54) PREPARATION OF ALKOXY- AND/OR HALOSILANE (POLY)SULFIDES AND COUPLING AGENTS COMPRISED THEREOF

(75) Inventors: Gérard Mignani, Lyons (FR); Samir Mansouri, Valencin (FR); Samuel Arthaud, Mornant (FR); Thierry Vidal, Lyons (FR)

(73) Assignee: Rhodia Operations, Aubervilliers (FR)

( * ) Notice: Subject to any disclaimer, the term of this patent is extended or adjusted under 35 U.S.C. 154(b) by 55 days.

This patent is subject to a terminal disclaimer.

(21) Appl. No.: 12/514,221

(22) PCT Filed: Nov. 9, 2007

(86) PCT No.: PCT/EP2007/062171
§ 371 (c)(1),
(2), (4) Date: Dec. 21, 2009

(87) PCT Pub. No.: WO2008/055989
PCT Pub. Date: May 15, 2008

(65) Prior Publication Data
US 2010/0144959 A1 Jun. 10, 2010

(30) Foreign Application Priority Data

Nov. 10, 2006 (FR) ...................................... 06 09838

(51) Int. Cl.
*C07F 7/04* (2006.01)

(52) U.S. Cl. ....................................... 556/478; 556/476
(58) Field of Classification Search ........................ None
See application file for complete search history.

(56) References Cited

U.S. PATENT DOCUMENTS

| | | | |
|---|---|---|---|
| 3,997,581 A | 12/1976 | Pletka et al. | |
| 5,580,919 A | 12/1996 | Agostini et al. | |
| 2005/0070731 A1* | 3/2005 | Guennouni et al. | 556/476 |

FOREIGN PATENT DOCUMENTS

| | | |
|---|---|---|
| DE | 2405758 A1 | 8/1975 |
| EP | 0785206 A1 | 1/1997 |
| WO | WO 03/027125 A1 | 4/2003 |

OTHER PUBLICATIONS

International Search Report PCT/EP2007/062171 dated May 23, 2008.

* cited by examiner

*Primary Examiner* — Sudhakar Katakam
(74) *Attorney, Agent, or Firm* — SNR Denton US LLP

(57) ABSTRACT

At least one (poly)thio alkoxy and/or halosilane is/are prepared by reaction of at least one sulfur-containing reagent with at least one alkoxy and/or halosilane, wherein an ionic addition of a sulfur-containing reagent to an alkoxy and/or halosilane is preferably conducted with thermal and/or actinic activation; the novel polythio alkoxy and/or halosilanes of formula (III.2) thus prepared are particularly useful as coupling agents in elastomeric compositions containing a white filler of the silica type and having the formula (III.2) wherein, for example, $R^{1.1}$ and $R^{1.3}$=methyl and $R^{1.2}$=ethoxy.

11 Claims, No Drawings

PREPARATION OF ALKOXY- AND/OR HALOSILANE (POLY)SULFIDES AND COUPLING AGENTS COMPRISED THEREOF

CROSS-REFERENCE TO PRIORITY/PCT APPLICATIONS

This application claims priority under 35 U.S.C. §119 of FR 0609838, filed Nov. 10, 2006, and is a continuation/national phase of PCT/EP 2007/062171, filed Nov. 9, 2007 and designating the United States (published in the French language on May 15, 2008, as WO 2008/055989 A2; the title and abstract were also published in English), each hereby expressly incorporated by reference in its entirety and each assigned to the assignee hereof.

The invention relates to a novel route for the synthesis of alkoxy-and/or halosilane (poly)sulfides. It also relates to certain alkoxy-and/or halosilane (poly)sulfides which are novel as such, for example capable of being obtained by this novel synthetic route.

The final products targeted are more specifically alkoxy-disilanes in which the two alkoxylated silane units are connected to one another via a (poly) sulfide bridge. These alkoxysilanes can be of use in particular as white filler/elastomer coupling agents in elastomer compositions comprising a white filler, in particular a siliceous material, as reinforcing filler.

The invention is also targeted at the elastomer compositions comprising such a coupling agent and articles based on one of these compositions.

The coupling agents of the invention can be of use particularly in the preparation of articles made of elastomer(s) which are subjected to various stresses, for example such as a variation in temperature, a high frequency loading variation under dynamic conditions, a high static load or a high bending fatigue under dynamic conditions. Examples of articles of this type consist of footwear soles, tires, conveyor belts, power transmission belting, flexible pipes, expansion joints, seals of domestic electrical appliances, supports which act to extract vibrations from engines, either with metal reinforcements or with hydraulic fluid inside the elastomer, cables, cable sheaths or cableway rollers. Elastomer compositions appropriate for the preparation of such articles should preferably exhibit the following properties:

good rheological properties, for example marked by viscosities which are as low as possible for great ease of processing of the uncured mixtures prepared, in particular with regard to extrusion and calendering operations;

rather short vulcanization times, in particular in order to achieve an excellent productive output for the vulcanization plant; and/or very good reinforcing properties conferred by a filler, for example optimum values for tensile modulus of elasticity and tensile strength.

In attempting to achieve such an objective, numerous solutions have been proposed which have essentially concentrated on the use of elastomer(s) modified with a reinforcing filler. It is known, generally, that, in order to obtain the optimum reinforcing properties conferred by a filler, it is advisable for the latter to be present in the elastomeric matrix in a final form which is both as finely divided as possible and as homogeneously distributed as possible. In point of fact, such conditions can only be achieved insofar as the filler exhibits a very good ability, on the one hand, to be incorporated in the matrix during the mixing with the elastomer(s) and to be deagglomerated and, on the other hand, to be homogeneously dispersed in the elastomeric matrix.

In a known way, carbon black is a filler which can exhibit such abilities but this is not generally the case for white fillers. The use of white reinforcing filler alone, in particular reinforcing silica alone, may prove to be inappropriate due to the low level of certain properties of the filler-comprising elastomeric compositions obtained and consequently of certain qualities of the articles employing these compositions. This is because, for reasons of reciprocal affinities, the particles of white filler, in particular of silica, generally have a tendency to agglomerate with one another in the elastomeric matrix. These filler/filler interactions have the harmful consequence of limiting the dispersion of the filler and thus of limiting the reinforcing properties to a level substantially below that which it would be theoretically possible to achieve if all the white filler-elastomer bonds capable of being created during the mixing operation were actually obtained. In addition, these interactions may also tend to increase the viscosity in the uncured state of the elastomer compositions and thus to render them more difficult to process than in the presence of carbon black.

It is known to a person skilled in the art that it is generally necessary to use a coupling agent, also known as bonding agent, which has in particular the function of providing the connection between the surface of particles of white filler and the elastomer(s), while facilitating the dispersion of this white filler within the elastomeric matrix.

The term "white filler-elastomer coupling agent" is understood to mean, in a known way, an agent capable of establishing a satisfactory connection, of chemical and/or physical nature, between the white filler and the elastomer; such a coupling agent, which is at least bifunctional, for example has the simplified general formula "Y—B—X", in which:

Y represents a functional group (Y functional group) which is capable of physically and/or chemically bonding to the white filler, it being possible for such a bond to be established, for example, between a silicon atom of the coupling agent and the surface hydroxyl (OH) groups of the white filler (for example the surface silanols, when silica is concerned);

X represents a functional group (X functional group) capable of physically and/or chemically bonding to the elastomer, for example via a sulfur atom;

B represents a hydrocarbon group which makes it possible to connect Y and X.

The coupling agents must in particular not be confused with simple white filler covering agents, which, in a known way, can comprise the Y functional group active with regard to the white filler but are devoid of the X functional group active with regard to the elastomer. Coupling agents, in particular silica-elastomer coupling agents, have been described in a large number of documents, the best known being bifunctional organoxysilanes carrying at least one organoxysilyl functional group as Y functional group and, as X functional group, at least one functional group capable of reacting with the elastomer, such as, in particular, a polysulfide functional group.

Thus, the proposal has been made to use, as organoxysilane polysulfides, alkoxysilane polysulfides, in particular bis(tri ($C_1$-$C_4$)alkoxylsilylpropyl)polysulfides, such as described in numerous patents or patent applications (for example FR-A-2 149 339, FR-A-2 206 330, U.S. Pat. Nos. 3,842,111, 3,873, 489 and 3,997,581). Mention may in particular be made, among these polysulfides, of bis(triethoxysilylpropyl)tetrasulfide (abbreviated to TESPT), which is generally still regarded today as the product contributing, for vulcanizates with silica as filler, the best compromise in terms of scorch safety, ease of processing and reinforcing power (for example, U.S. Pat. Nos. 5,652,310, 5,684,171 and 5,684,172). However, one of the disadvantages relating to the use of TESPT lies in its manufacture. This is because TESPT can be obtained in three synthetic stages by using a hydrochlorosilane as base starting material, which reactant is extremely problematic to handle for reasons of safety. Furthermore, the reaction employing the hydrochlorosilane is a hydrosilylation reaction catalyzed by a precious metal, the selectivity of which remains modest and which results in the formation of a coproduct.

During the preparation of the elastomer compositions comprising particles of reinforcing white filler and a coupling agent of organoxysilane polysulfide type, there may occur, for example during the stage of kneading in a conventional internal mixer, a chemical reaction involving the organoxy portion of the silane and the surface OH groups of the white filler, for example the surface silanols when silica is concerned.

As described in the literature (A. Hunsche et al., Kautschuk Gummi, Kunststoffe, 80, 881 (1997), and Kautschuk Gummi, Kunststoffe, No. 7-8, 525 (1998)), in the case of silica and TESPT, this chemical reaction is a condensation reaction which is accompanied by a significant release of ethanol; more specifically, this chemical reaction, when organoxysilanes, such as TESPT, carrying three ethoxy functional groups bonded to the silicon are used, releases up to 3 moles of ethanol per mole of silane. This released alcohol is generally the cause of technical problems during the subsequent transformation of the elastomer compositions, for example marked by the appearance of an undesirable porosity during in particular extrusion of said compositions and/or the undesirable formation of bubbles in the elastomer itself. Moreover, a reduction in the release of alcohol may also be desirable for ecological and health reasons.

The proposal has been made, in patent EP 1 043 357, to reduce the release of alcohol by employing an organoxysilane polysulfide coupling agent having a reduced number of organoxy functional groups, such as, for example, ethoxy functional groups, carried by the silicon in comparison with the coupling agents normally used, such as bis(triethoxysilylpropyl)disulfide (abbreviated to TESPD), which carries three ethoxy functional groups. Thus, bis(monoethoxydimethylsilylpropyl)disulfide (abbreviated to MESPD) may make it possible to reduce the amount of alcohol released in comparison with TESPD but it results, in the vulcanizates obtained, in particular in a significant deterioration in some of their mechanical properties. Application WO-A-02/083719 describes monoorganoxysilane polysulfides with a propylene linking unit of formula F:

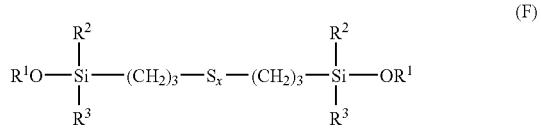

(F)

in which the $R^1$, $R^2$ and $R^3$ symbols are monovalent hydrocarbon groups and x is a number ranging from 3±0.1 to 5±01. These compounds can be used as white filler-elastomer coupling agents in diene rubber compositions comprising a white filler, such as a siliceous material, as reinforcing filler.

One of the objectives of the present invention is to provide an alternative route of access to alkoxysilane and halosilane, in particular monoalkoxysilane, polysulfides, especially those as defined by the formula (F) targeted above.

Another objective of the invention is that this alternative route for the synthesis of alkoxysilane polysulfide preferably be simple and economic to implement.

Another objective of the present invention is to provide novel alkoxysilane, in particular monoalkoxysilane, polysulfides with a specific alkylene (preferably isopropylene) linking unit comprising at least two alkoxysilane poles connected to one another via a polysulfide unit and via two specific alkylene (preferably isopropylene) linking units on either side of this "polysulfide" bridge.

Another object of the invention is to provide novel alkoxy- and/or halosilane (poly)sulfides, in particular monoalkoxysilane polysulfides, with a specific alkylene linking unit (preferably with an isopropylene linking unit) which can especially be used as white filler-elastomer coupling agents in elastomer compositions comprising a white filler, in particular a siliceous material, as reinforcing filler, these novel coupling agents advantageously being effective and economic.

These objectives, among others, are achieved by the present invention, which relates, in its first subject matter, to a process for the preparation of at least one alkoxy-and/or halosilane (poly)sulfide, characterized in that it essentially comprises reacting, according to an ionic addition mechanism, at least one sulfur-comprising reactant (Rs) with at least one alkoxy-and/or halosilane of formula (I):

(I)

in which:
the $R^1$ symbols, which are identical or different, each represent:
a linear, branched or cyclic alkyl radical having from 1 to 20 carbon atoms;
an aryl radical having from 6 to 18 carbon atoms;
an —$OR^2$ alkoxy radical, with $R^2$ corresponding to a linear, branched or cyclic alkyl radical having from 1 to 20 carbon atoms or an aryl radical having from 6 to 18 carbon atoms;
an arylalkyl radical or an alkylaryl radical ($C_6$-$C_{18}$ aryl, $C_1$-$C_{20}$ alkyl)
a hydroxyl (—OH) radical;
or a halogen, preferably chlorine;
at least one of these $R^1$ radicals being —$OR^2$, —OH or a halogen and, in addition, these $R^1$ radicals, when they are neither hydroxyl nor halogens, optionally carrying at least one halogenated group;
the Y symbol represents a monovalent organic functional group preferably chosen from "sensitive" $R^3$ functional groups comprising at least one ethylenic and/or acetylenic unsaturation selected in particular from:
linear, branched or cyclic $R^{3.1}$ alkenyl groups having from 2 to 10 carbon atoms,
linear, branched or cyclic $R^{3.2}$ alkynyl groups having from 2 to 10 carbon atoms,
linear, branched or cyclic $R^{3.3}$-(alkenyl-alkynyl) or -(alkynyl-alkenyl) groups having from 5 to 20 carbon atoms,
the $R^{3.1}$ radicals being particularly preferred,
and Y in addition being able optionally to comprise at least one heteroatom and/or to carry one or more aromatic groups.

Preferably, the silane of formula (I) is such that at least one (better still just one) of the $R^1$ radicals is —$OR^2$.

The invention also relates, in its second subject matter, to novel alkoxy-and/or halosilane (poly)sulfides of formula (III):

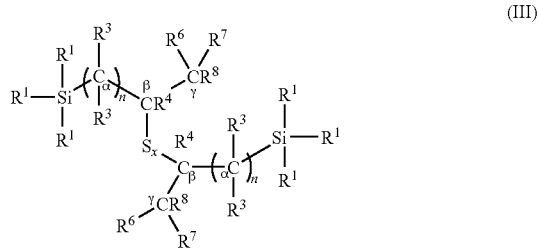

(III)

in which:
- the $R^1$ symbols, which are identical or different, each represent:
  - a linear, branched or cyclic alkyl radical having from 1 to 20 carbon atoms;
  - an aryl radical having from 6 to 18 carbon atoms;
  - an —$OR^2$ alkoxy radical, with $R^2$ corresponding to a linear, branched or cyclic alkyl radical having from 1 to 20 carbon atoms or an aryl radical having from 6 to 18 carbon atoms;
  - an arylalkyl radical or an alkylaryl radical ($C_6$-$C_{18}$ aryl, $C_1$-$C_{20}$ alkyl)
  - a hydroxyl (—OH) radical;
  - or a halogen, preferably chlorine;
  - at least one of these $R^1$ radicals being —$OR^2$, —OH or a halogen and, in addition, these $R^1$ radicals, when they are neither hydroxyl nor halogens, optionally carrying at least one halogenated group;
- the $R^3$ and $R^4$ symbols, which are identical to or different from one another, each represent hydrogen or a monovalent hydrocarbon group chosen from a linear, branched or cyclic alkyl radical having from 1 to 20 carbon atoms or a linear, branched or cyclic alkoxyalkyl radical having from 1 to 20 carbon atoms;
- the $R^6$, $R^7$ and $R^8$ symbols, which are identical to or different from one another, each represent hydrogen or a monovalent hydrocarbon group chosen from a linear, branched or cyclic alkyl radical having from 1 to 20 carbon atoms and a linear, branched or cyclic alkoxyalkyl radical having from 1 to 20 carbon atoms,
- the n symbol corresponds to an integer greater than or equal to 1, preferably equal to 1 or 2, more preferably still equal to 1 (the formula (III) is then in the latter case denoted formula (III.1)),
- the x symbol corresponds to an integer or a fractional number generally of between 1 and 10, preferably between 1 and 5 and more preferably still between 1.5 and 5, in particular between 2 and 5, especially between 3 and 5, indeed even between 3.5 and 4.5 or between 3.8 and 4.2, the limits of these intervals being given to within ±0.2.

These novel alkoxy-and/or halosilane (poly)sulfides of formula (III), in particular formula (III.1), can be, and this preferably, obtained by the process according to the invention.

The invention also relates, in its third subject matter, to the use of at least one alkoxy-and/or halosilane polysulfide of formula (III) (in particular of formula (III.1)), in particular of at least one silane polysulfide of formula (III.1) with an isopropylene linking unit, as white filler-elastomer coupling agent in elastomer compositions preferably comprising at least one diene elastomer and a white filler (in particular a precipitated silica) as reinforcing filler, said compositions being, for example, intended for the manufacture of articles made of diene elastomer(s).

In its fourth subject matter, the present invention relates to an elastomer, in particular diene elastomer, composition comprising a reinforcing white filler and an effective amount of at least one alkoxy-and/or halosilane polysulfide of formula (III) (in particular of formula (III.1)), especially a monoorganoxysilane polysulfide of formula (III.1) with an isopropylene linking unit.

In a fifth subject matter, the invention relates to a process for the preparation of the elastomer compositions targeted above.

In a sixth subject matter, the invention relates to articles made of elastomer(s) based on an elastomer composition targeted above.

First Subject Matter of the Invention

It is to the credit of the inventors to have provided a novel synthetic route which is radically different from the synthetic routes known for the preparation of alkoxysilane polysulfides, which routes consisted in reacting an alkoxysilane with sulfur-comprising reactants.

In contrast to this, the invention provides for the reaction of a functionalized alkoxy-and/or halosilane (I), preferably an alkenylated alkoxy-and/or halosilane, for example an alkoxy-and/or halosilane with an allyl ending, with a sulfur-comprising reactant (Rs).

The novel route according to the invention is based on an ionic addition mechanism which is easy to implement and economic.

(Rs) and (I) are reacted according to an ionic addition mechanism.

In addition, entirely surprisingly and unexpectedly, this ionic addition mechanism is (quasi)spontaneous. It does not require activation, in particular actinic activation (photon activation: for example a vessel under a UV lamp, in particular of Hg—HP type) and/or thermal activation and/or ultrasonic activation and/or activation by electron bombardment.

The fact remains nonetheless that it is entirely possible, according to an alternative form of the invention, to provide such activation, in particular actinic activation (photon activation: for example a vessel under a UV lamp, in particular of Hg—HP type) and/or thermal activation and/or ultrasonic activation and/or activation by electron bombardment. In practice, it is preferable to employ thermal activation, which generally consists in bringing the reaction medium to a temperature of between ambient temperature and 120° C., preferably between 50 and 110° C., for standard atmospheric pressure.

This novel synthetic route is simple and nonrestricting industrially.

Such a synthetic route makes it possible in addition to result in novel alkoxysilane and/or halosilane (poly) sulfides.

The silane polysulfides obtained by the process according to the invention, inter alia the novel silane polysulfides, have in particular applications as white filler-elastomer coupling agents in elastomer, in particular diene elastomer, composition(s) comprising a white filler, for example a siliceous filler, as reinforcing filler, these compositions being, for example, intended for the manufacture of articles made of elastomers, in particular diene elastomer(s), such as, inter alia, footwear soles or tires.

Such coupling agents preferably confer good mechanical properties on the elastomers comprising siliceous material as filler in which they are incorporated.

It is the same concerning their rheological characteristics before vulcanization.

The good mechanical properties after vulcanization can be reflected by rather high levels of moduli at high elongations, of tear strength, of reinforcing indices and/or of hardness (shore or other).

They thus offer a good compromise as regards the rheological properties before vulcanization and the mechanical properties after vulcanization.

The alkoxy-and/or halosilane (poly)sulfides obtained by the process according to the invention advantageously comprise an $[S]_x$ polysulfide unit.

According to a preferred characteristic of the invention, Y corresponds to the following formula (II):

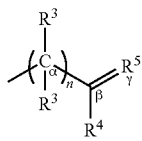

(II)

in which:
the $R^3$ and $R^4$ symbols, which are identical to or different from one another, each represent hydrogen or a monovalent hydrocarbon group chosen from a linear, branched or cyclic alkyl radical having from 1 to 20 carbon atoms and a linear, branched or cyclic alkoxyalkyl radical having from 1 to 20 carbon atoms;
the $R^5$ symbol represents $CH_2$ or $CR^6R^7$, the $R^6$ and $R^7$ symbols, which are identical to or different from one another, each representing hydrogen or a monovalent hydrocarbon group chosen from a linear, branched or cyclic alkyl radical having from 1 to 20 carbon atoms and a linear, branched or cyclic alkoxyalkyl radical having from 1 to 20 carbon atoms, methyl being particularly preferred;
the n symbol corresponds to an integer greater than or equal to 1, preferably equal to 1 or 2, more preferably still equal to 1 (the formula (II) is then in the latter case denoted formula (II.1)).

Thus, according to an even more preferred characteristic of the invention, Y corresponds to the following formula (II.1):

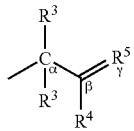

(II.1)

in which:
the $R^3$ and $R^4$ symbols, which are identical to or different from one another, each represent hydrogen or a monovalent hydrocarbon group chosen from a linear, branched or cyclic alkyl radical having from 1 to 20 carbon atoms and a linear, branched or cyclic alkoxyalkyl radical having from 1 to 20 carbon atoms;
the $R^5$ symbol represents $CH_2$ or $CR^6R^7$, the $R^6$ and $R^7$ symbols, which are identical to or different from one another, each representing hydrogen or a monovalent hydrocarbon group chosen from a linear, branched or cyclic alkyl radical having from 1 to 20 carbon atoms and a linear, branched or cyclic alkoxyalkyl radical having from 1 to 20 carbon atoms, methyl being particularly preferred.

The Y functional group of the alkoxy-and/or halosilane (I) forming the starting material of the process according to the invention proves to be a precursor of the linking unit(s) which connect(s) the silicon to the sulfur-comprising unit in the alkoxy-and/or halosilane (poly)sulfides obtained.

According to a first embodiment of the process according to the invention, $R^4$ corresponds to H and $R^5$ corresponds to $CH_2$, so that the (ionic) addition of (Rs) takes place on the beta (β) carbon of the alkoxy-and/or halosilane (I).

According to a second embodiment of the process according to the invention, $R^4$ corresponds to an alkyl radical (preferably a methyl or ethyl radical) and $R^5$ corresponds to $CH_2$, so that the addition of (Rs) takes place on the beta (β) carbon of the alkoxy-and/or halosilane (I).

Generally, the addition to the beta (β) carbon of the alkoxy-and/or halosilane (I) results, by the process according to the invention, in novel alkoxy-and/or halosilane (poly)sulfides.

According to a third embodiment of the process according to the invention, $R^4$ corresponds to H and $R^5$ corresponds to $CR^6R^7$ with $R^6$ and $R^7$ representing —$CH_3$, so that the (ionic) addition of (Rs) takes place on the gamma (γ) carbon of the alkoxy-and/or halosilane (I). Particularly advantageously and surprisingly, the (ionic) addition according to the invention of the Y alkenyl ending of formula (II), preferably of formula (II.1), of the silane (I) benefits from complete regioselectivity and a high isolated yield, for example of greater than 90%: this complete regioselectivity means that the double bond of the Y radical reacts with the sulfur-comprising reactant (Rs) without side reaction.

Alkoxysilane or halosilane of formula (I) used in the process according to the invention can be obtained by reacting at least one halo-and/or alkoxysilane with at least one halogenated organic compound, preferably an allyl halide, in the presence of at least one metal chosen from the group consisting of Mg, Na, Li, Ca, Ba, Cd, Zn, Cu, their mixtures and their alloys (preferably magnesium), in the presence of an ethereal organic solvent and/or a solvent of acetal type, according to a mechanism based on the Barbier reaction.

Another route for the synthesis of the starting alkoxy-and/or halosilane of formula (I) can be a more conventional route, in particular in which use is made of a trialkoxysilane and/or a trihalosilane functionalized by a halogenated alkyl group, according to a reaction mechanism of Grignard type which involves a halomagnesium Grignard reagent, namely MeMgCl. This synthetic route is described in particular in applications JP-A-2002179687 and WO-A-03/027125.

According to another advantageous form of the process according to the invention, the sulfur-comprising reactant (Rs) is chosen from the group consisting of $HS_xH$, O,O'-dialkyl (preferably O,O'-diethyl)dithiophosphate HSPS), $M'_2S_x$ (M' being an alkali metal), xS, H—$S_x$ and their mixtures, the x symbol corresponding to an integer or fractional number, preferably a number ranging from 1 to 10, more preferably still from 1 to 5, in particular from 1.5 to 5, the limits of these intervals being given to within ±0.2.

These reactants (Rs) are inexpensive and readily available.

Thus, the reactants (Rs) of polysulfane ($HS_xH$) type can, for example, be prepared according to a procedure described in the literature, in particular by W. Post et al., J. Org. Chem., 24 (1959), 492, and by E. Mular et al., Can. J. Chem., 46 (1968), 2341.

In practice, the salt Na$_2$S$_x$ can be reacted with dilute HCl at ambient temperature according to the following general reaction:

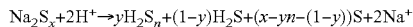

$$Na_2S_x + 2H^+ \rightarrow yH_2S_n + (1-y)H_2S + (x-yn-(1-y))S + 2Na^+ \qquad 5$$

After separation by settling, an odorous yellow oil is obtained, the $^1$H NMR and Raman analyses of which confirm the structure.

In the case where (Rs) is of M'$_2$S$_x$ type, this metal polysulfide can be prepared, for example, by reaction of an alkaline sulfide M'$_2$S, comprising water of crystallization, with elemental sulfur, the operation being carried out at a temperature of between 60 and 300° C. under vacuum and in the absence of organic solvent.

According to an alternative embodiment of the invention in which (Rs) corresponds to O,O'-dialkyl (preferably O,O'-diethyl)dithiophosphate (HSPS) or to HSH, the product of the reaction between (I) and (Rs) is reacted with a secondary sulfur-comprising reactant (Rs2) chosen from the group consisting of S$_x$ and/or X1S—SX2, with the x symbol as defined above and X1 and X2 representing a halogen, preferably chlorine, this secondary sulfurization advantageously being carried out in a basic medium for example comprising, as base, K$_2$CO$_3$, Na$_2$CO$_3$, K$_3$PO$_4$, EtONa or their mixtures.

In this alternative form, the product of the reaction between (I) and (Rs) is a monosilane sulfide which can be converted to a disilane polysulfide using the secondary sulfur-comprising reactant (Rs2).

Apart from the qualitative aspects with regard to the nature of the silane (I) and the sulfur-comprising reactant (Rs), the process according to the invention also incorporates advantageous quantitative aspects. Thus it is that the (I)/(Rs) molar ratio is in particular between 5 and 0.1, preferably between 3 and 0.5 and more preferably still between 2 and 0.7.

According to an alternative form, the (ionic) addition of the process according to the invention can be carried out in the presence of solvent(s) preferably chosen from the group consisting of unreactive hydrocarbon solvents, in particular chosen from aromatic hydrocarbons devoid of carbonyl or hydroxyl functional groups.

The process according to the invention can, for example, be carried out at atmospheric pressure.

(Rs) can be run onto a heel of (I), for example between 50 and 70° C.

The reaction medium obtained can be treated by filtering off the possible residual sulfur, washing with an organic solvent, such as heptane, then washing the filtrate with an aqueous solution, in particular with a pH of between 7 and 8, it being possible for the organic solvent, such as heptane, to be subsequently removed under reduced pressure.

The process according to the invention can comprise at least one hydrolysis stage which makes it possible to convert at least one of the R$^1$ radicals corresponding to —OR$^2$ of the alkoxy-and/or halosilane (poly)sulfide to a hydroxyl (—OH).

Second Subject Matter of the Invention

The novel synthetic route provided in the first subject matter of the invention as described above is also highly advantageous in that it makes it possible to result in novel alkoxy-and/or halosilane (poly)sulfides.

In its second subject matter, the invention is thus targeted at novel alkoxy-and/or halosilane (poly)sulfides of formula (III), whether or not obtained by the process in accordance with the first subject matter of the invention.

More particularly, the invention is targeted, in its second subject matter, at novel alkoxy-and/or halosilane (poly)sulfides of following formula (III.1), whether or not obtained by the process in accordance with the first subject matter of the invention:

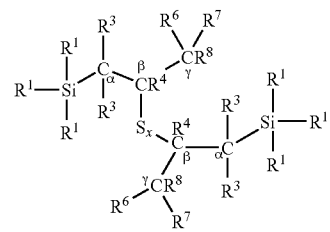

(III.1)

in which:
the R$^1$ symbols, which are identical or different, each represent:
a linear, branched or cyclic alkyl radical having from 1 to 20 carbon atoms;
an aryl radical having from 6 to 18 carbon atoms;
an —OR$^2$ alkoxy radical, with R$^2$ corresponding to a linear, branched or cyclic alkyl radical having from 1 to 20 carbon atoms or an aryl radical having from 6 to 18 carbon atoms;
an arylalkyl radical or an alkylaryl radical (C$_6$-C$_{18}$ aryl, C$_1$-C$_{20}$ alkyl);
a hydroxyl (—OH) radical;
or a halogen, preferably chlorine;
at least one of these R$^1$ radicals being —OR$^2$, —OH or a halogen and, in addition, these R$^1$ radicals, when they are neither hydroxyl nor halogens, optionally carrying at least one halogenated group;
the R$^3$ and R$^4$ symbols, which are identical to or different from one another, each represent hydrogen or a monovalent hydrocarbon group chosen from a linear, branched or cyclic alkyl radical having from 1 to 20 carbon atoms or a linear, branched or cyclic alkoxyalkyl radical having from 1 to 20 carbon atoms;
the R$^6$, R$^7$ and R$^8$ symbols, which are identical to or different from one another, each represent hydrogen or a monovalent hydrocarbon group chosen from a linear, branched or cyclic alkyl radical having from 1 to 20 carbon atoms and a linear, branched or cyclic alkoxyalkyl radical having from 1 to 20 carbon atoms,
the x symbol corresponds to an integer or a fractional number generally of between 1 and 10, preferably between 1 and 5 and more preferably still between 1.5 and 5, in particular between 2 and 5, especially between 3 and 5, indeed even between 3.5 and 4.5 or between 3.8 and 4.2, the limits of these intervals being given to within ±0.2.

The (III), in particular (III.1), products can in addition be distinguished by their preferred method of preparation according to the process in accordance with the invention; they then advantageously result from an ionic addition of (Rs) to the β carbon of the Y group (formula (II), in particular (II.1)) of the silane (I). The alkoxy-and/or halosilane (poly)sulfides of formula (III), in particular (III.1), are preferably capable of being prepared by the process according to the invention (in particular by ionic addition of (Rs) to the β carbon of the Y group (formula III), in particular (II.1)) of the silane (I).

In a preferred embodiment, two of the R$^1$ substituents of at least one of the two end silicons are alkyl radicals, preferably methyl, ethyl, n-propyl, isopropyl, n-butyl, CH$_3$O—CH$_2$— and $CH_3O—CH(CH_3)CH_2—$ radicals (for example, methyl, ethyl, n-propyl and isopropyl radicals), or aryl radicals, for example phenyl radicals, these two $R^1$ substituents preferably being methyl; the third $R^1$ substituent is preferably an $—OR^2$ alkoxy, in particular with $R^2$ corresponding to methyl, ethyl, n-propyl, isopropyl, n-butyl, $CH_3O—CH_2—$ or $CH_3O—CH(CH_3)CH_2—$ (for example, methyl, ethyl, n-propyl or isopropyl).

The products of formula (III), in particular of formula (III.1), which are especially targeted by the present invention are alkoxysilane (poly)sulfides, more particularly alkoxysilane (poly)sulfides of formula (III.2):

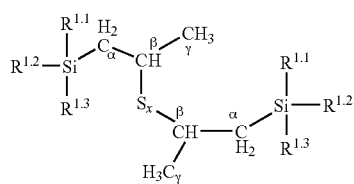

(III.2)

in which the $R^{1.1}$, $R^{1.2}$ and $R^{1.3}$ symbols, which are identical to or different from one another, correspond to one of the definitions given in the above account for $R^1$; $R^{1.1}$ and $R^{1.3}$ preferably corresponding to an alkyl (advantageously methyl or ethyl) and $R^{1.2}$ preferably corresponding to an alkoxy (advantageously methoxy or ethoxy), the x symbol corresponding to an integer or a fractional number generally of between 1 and 10, preferably between 1 and 5 and more preferably still between 1.5 and 5, in particular between 2 and 5, especially between 3 and 5, indeed even between 3.5 and 4.5 or between 3.8 and 4.2, the limits of these intervals being given to within ±0.2.

The present invention relates, for example, to the compounds of following formulae:

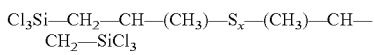

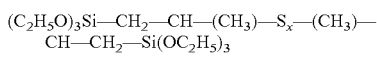

in which the x symbol corresponds to an integer or fractional number of between 1.5 and 5, in particular between 2 and 5, especially between 3 and 5, for example between 3.5 and 4.5 or between 3.8 and 4.2, the limits of these ranges being given to within ±0.2. Particularly preferred compounds according to the invention exhibit the formula $(C_2H_5O)(CH_3)_2Si—CH_2—CH—(CH_3)—S_x—(CH_3)—CH—CH_2—Si(CH_3)_2(OC_2H_5)$, in which the x symbol corresponds to an integer or fractional number between 1.5 and 5, preferably between 2 and 5, in particular between 3 and 5, for example between 3.5 and 4.5 or between 3.8 and 4.2, the limits of these ranges being given to within ±0.2; mention may in particular be made of bis(monoethoxydimethylsilylisopropyl)tetrasulfide (abbreviated to MESiPrT).

The x symbol of the formulae (III), (III.1) and (III.2) and of the above formulae is an integer or fractional number which represents the number of sulfur atoms present in a molecule of these formulae.

This number can be an exact number of sulfur atoms, in the case where the route for the synthesis of the compound under consideration can give rise only to a single type of polysulfide product.

In practice, this number is instead the mean of the number of sulfur atoms per molecule of compound under consideration, insofar as the chosen synthetic route gives rise instead to a mixture of polysulfide products each having a different number of sulfur atoms. In this case, the polysulfide compounds synthesized are in fact composed of a distribution of polysulfides ranging from the monosulfide or the disulfide $S_2$ to heavier polysulfides (for example $S_{\geq 5}$) centered on a mean molar value (value of the x symbol) lying within the general regions mentioned above. Advantageously, the monoorganoxysilane polysulfides synthesized are composed of a distribution of polysulfides comprising a molar level: of $(S_3+S_4)$ equal to or greater than 40% and preferably equal to or greater than 50%; and of $(S_2+S_{\geq 5})$ equal to or less than 60% and preferably equal to or less than 50%. Furthermore, the molar level of $S_2$ is advantageously equal to or less than 30% and preferably equal to or less than 20%. All the limit values are given within the accuracy of measurement (by NMR), with an absolute error of approximately ±1.5 (for example 20±1.5% for the final level shown).

As mentioned above, these novel products may find a particularly advantageous application as agents for coupling between a white filler (such as a siliceous material, for example a precipitated silica) and an elastomer in elastomer compositions, in particular diene elastomer compositions, which comprise such a white filler as reinforcing filler. They constitute an alternative to the coupling agents of the state of the art. These novel (III) compounds, in particular (III.1) compounds, especially (III.2) compounds, preferably offer a very satisfactory compromise with regard to the rheological properties before vulcanization and the mechanical and/or dynamic properties after vulcanization.

Third Subject Matter of the Invention

In its third subject matter, the invention relates to the use of at least one silane polysulfide of formula (III), preferably of formula (III.1), in particular of formula (III.2), as white filler-elastomer coupling agent in elastomer compositions, for example diene elastomer compositions, in particular comprising at least one diene elastomer and a white filler (in particular a precipitated silica) as reinforcing filler, said compositions being intended, for example, for the manufacture of articles made of elastomer(s), in particular diene elastomer(s).

Fourth Subject Matter of the Invention

According to its fourth subject matter, the present invention lies in elastomer compositions, in particular diene elastomer compositions, comprising a reinforcing white filler and, as coupling agent, (an effective amount of) at least one silane polysulfide of formula (III), preferably of formula (III.1), in particular of formula (III.2).

More particularly, these compositions can comprise (the parts being given by weight), per 100 parts of diene elastomer(s):
  10 to 200 parts, preferably 20 to 150 parts and more preferably still 30 to 100 parts of reinforcing white filler and
  1 to 20 parts, preferably 2 to 20 parts and more preferably still 2 to 12 parts of coupling agent(s).

Advantageously, the amount of coupling agent(s), chosen in particular within the abovementioned ranges, is determined so that it represents from 0.5 to 20%, preferably from 1 to 15% and more preferably from 1 to 10%, with respect to the weight of the reinforcing white filler.

In the context of the invention, the use of a compound of formula (III), preferably of formula (III.1), in particular of formula (III.2), can in addition make it possible to dispense, completely or virtually completely, with the presence of a zinc or of a zinc derivative (such as ZnO) normally employed as vulcanization activator in elastomer composition(s), in particular diene elastomer composition(s), comprising such a (III) compound, preferably (III.1) compound, especially (III.2) compound, and a reinforcing white filler which are intended, for example, for the manufacture of articles made of elastomer(s), in particular diene elastomer(s).

Said elastomer compositions according to the invention can, for example, comprise less than 0.75 part, in particular less than 0.5 part, of zinc (per 100 parts of (diene) elastomer(s)).

A person skilled in the art will understand that the coupling agent can be grafted beforehand to the reinforcing white filler (via in particular its alkoxysilyl functional group, for example ethoxysilyl functional group), it being possible for the white filler, thus "precoupled", subsequently to be bonded to the elastomer via the free polysulfide functional group.

In the present account, the expression "reinforcing white filler" is intended to define in particular a white filler capable of reinforcing by itself alone, without means other than that of a coupling agent, a composition formed of elastomer(s) of natural and/or synthetic rubber type.

The physical state under which the reinforcing white filler is provided is not important, that is to say that said filler can be provided, for example, in the form of a powder, microbeads or granules.

Preferably, the reinforcing white filler consists of silica, alumina or a mixture of these two entities.

More preferably, the reinforcing white filler is formed by silica.

All precipitated or pyrogenic silicas, in particular those exhibiting a BET specific surface of less than or equal to 450 m$^2$/g, are suitable in particular as silica capable of being employed in the invention.

According to a highly advantageous alternative form, use is made of a precipitated silica, it being possible for the latter to be conventional or, preferably, highly dispersible.

The term "highly dispersible silica" is understood to mean in particular any silica having a very high ability to deagglomerate and to disperse in a polymer matrix which can be observed in particular by electron or optical microscopy, on thin sections.

It is possible, for example, to employ a highly dispersible silica exhibiting a CTAB specific surface equal to or less than 450 m$^2$/g, in particular of between 50 and 350 m$^2$/g.

It is possible to employ a silica in accordance with one of applications EP-A-05 20 862, WO-A-95/09127, WO-A-95/09128, WO-A-98/54090 and WO-A-03/016215.

Mention may be made, as nonlimiting examples of dispersible silicas, of the silica Perkasil KS 430 from Akzo, the silicas BV3380 and Ultrasil 7000 from Degussa, the silicas Zeosil 1165 MP and 1115 MP from Rhodia, the silica Hi-Sil 2000 from PPG and the silicas Zeopol 8741 and 8745 from Huber.

Treated precipitated silicas, such as, for example, the aluminum-comprising silicas described in patent applications EP-A-0 735 088, 0 762 992 and 0 762 993, are also suitable.

The precipitated silicas having:
a CTAB specific surface of between 100 and 240 m$^2$/g, for example between 110 and 180 m$^2$/g,
a BET specific surface of between 100 and 250 m$^2$/g, for example between 110 and 190 mg$^2$/g,
optionally a DOP oil uptake of less than 300 ml/100 g, for example of between 200 and 295 ml/100 g, and
optionally a BET specific surface/CTAB specific surface ratio of between 1.0 and 1.6,
are more particularly highly suitable.

The term "silica" is also understood to mean blendings of different silicas.

The CTAB specific surface is the external surface which can be determined according to the NF T 45007 method (November 1987). The BET specific surface can be measured according to the Brunauer-Emmett-Teller method described in "The Journal of the American Chemical Society", vol. 60, page 309 (1938), which corresponds to the NF T 45007 standard (November 1987). The DOP oil uptake can be determined according to the ISO 787/5 standard by employing dioctyl phthalate.

Use may be made, as reinforcing alumina, of a dispersible alumina having:
a BET specific surface of between 30 and 400 m$^2$/g, for example between 60 and 250 m$^2$/g,
a mean particle size at most equal to 500 nm, for example at most equal to 200 nm, and
a high level of Al—OH reactive surface functional groups, such as described in patent application EP-A-0 810 258.

Mention may in particular be made, as nonlimiting examples of reinforcing aluminas, of the aluminas A125, CR125 and D65CR from Baikowski.

The expression "diene elastomers capable of being employed in the compositions in accordance with the fourth subject matter of the invention" is understood to mean more specifically:
(1) the homopolymers obtained by polymerization of a conjugated diene monomer having from 4 to 22 carbon atoms, such as, for example: 1,3-butadiene, 2-methyl-1,3-butadiene, 2,3-dimethyl-1,3-butadiene, 2,3-diethyl-1,3-butadiene, 2-methyl-3-ethyl-1,3-butadiene, 2-chloro-1,3-butadiene, 2-methyl-3-isopropyl-1,3-butadiene, 1-phenyl-1,3-butadiene, 1,3-pentadiene or 2,4-hexadiene;
(2) the copolymers obtained by copolymerization of at least two of the abovementioned conjugated dienes with one another or by copolymerization of one or more of the abovementioned conjugated dienes with one or more ethylenically unsaturated monomers chosen from:
vinylaromatic monomers having 8 to 20 carbon atoms, such as, for example: styrene, ortho-, meta-or para-methylstyrene, the "vinyl-toluene" commercial mixture, para-tert-butylstyrene, methoxystyrenes, chloro-styrenes, vinylmesitylene, divinylbenzene or vinyl naphthalene;
vinyl nitrile monomers having from 3 to 12 carbon atoms, such as, for example, acrylonitrile or methacrylonitrile;
acrylic ester monomers derived from acrylic acid or from methacrylic acid with alkanols having from 1 to 12 carbon atoms, such as, for example, methyl acrylate, ethyl acrylate, propyl acrylate, n-butyl acrylate, isobutyl acrylate, 2-ethylhexyl acrylate, methyl methacrylate, ethyl methacrylate, n-butyl methacrylate or isobutyl methacrylate;
it being possible for the copolymers to comprise between 99 and 20% by weight of diene units and between 1 and 80% by weight of vinylaromatic, vinyl nitrile and/or acrylic ester units;
(3) the ternary copolymers obtained by copolymerization of ethylene and of an α-olefin having from 3 to 6 carbon atoms with a nonconjugated diene monomer having from 6 to 12 carbon atoms, such as, for example, the elastomers obtained from ethylene and from propylene with a nonconjugated diene monomer of the above-mentioned type, such as, in particular, 1,4-hexadiene, ethyl idenenorbornene or dicyclopentadiene (EPDM elastomer);
(4) natural rubber;
(5) the copolymers obtained by copolymerization of isobutene and of isoprene (butyl rubber) and also the halogenated versions, in particular the chlorinated or brominated versions, of these copolymers;

(6) a blend of several of the abovementioned elastomers (1) to (5).

Use is preferably made of one or more elastomer(s) chosen from: (1) polybutadiene, polychloroprene, polyisoprene [or poly(2-methyl-1,3-butadiene)]; (2) poly(isoprene-butadiene), poly(isoprene-styrene), poly(isoprene-butadiene-styrene), poly(butadiene-styrene) or poly(butadiene-acrylonitrile); (4) natural rubber; (5) butyl rubber; (6) a blend of the abovementioned elastomers (1), (2), (4) and (5) with one another; (6') a blend comprising a predominant amount (ranging from 51 to 99.5% by weight and preferably from 70 to 99% by weight) of polyisoprene (1) and/or of natural rubber (4) and a minor amount (ranging from 49 to 0.5% by weight and preferably from 30 to 1% by weight) of polybutadiene, of polychloroprene, of poly(butadiene-styrene) and/or of poly(butadiene-acrylonitrile).

The compositions in accordance with the invention additionally comprise all or a portion of the other constituents and auxiliary additives commonly used in the field of elastomer and/or rubber compositions.

Thus, it is possible to employ all or a portion of the other constituents and additives which follow:
as regards the vulcanization system, mention may be made, for example:
of vulcanization agents chosen from sulfur or sulfur-donating compounds, such as, for example, thiuram derivatives;
of vulcanization accelerators, such as, for example, guanidine derivatives or thiazole derivatives;
of vulcanization activators, such as, for example, zinc oxide, stearic acid and zinc stearate;
as regards other additive(s), mention may be made, for example:
of a conventional reinforcing filler composed of carbon black; all carbon blacks, in particular those of the HAF, ISAF or SAF type, are suitable as carbon blacks; mention may be made, as nonlimiting examples, of N115, N134, N234, N339, N347 and N375 carbon blacks; generally, the amount of carbon black is determined so that, on the one hand, the reinforcing white filler employed represents more than 50% of the weight of the white filler+carbon black combination and, on the other hand, the total amount of reinforcing filler (white filler+carbon black) remains within the intervals of values indicated above for the reinforcing white filler in connection with the make-up by weight of the composition;
of a conventional white filler which is nonreinforcing or only slightly reinforcing, such as, for example, clays, bentonite, talc, chalk, kaolin, titanium dioxide or a mixture of these entities;
of antioxidants or antiozonants, such as, for example, N-phenyl-N'-(1,3-dimethylbutyl)-p-phenylenediamine;
of plasticizing agents and processing aids.

As regards the processing aids, the compositions in accordance with the invention can comprise covering agents for the reinforcing filler, for example comprising just the Y functional group, which are capable, in a known way, by virtue of an improvement in the dispersion of the filler in the elastomer matrix and of a lowering in the viscosity of the compositions, of improving the processing property of the compositions in the uncured state. Such agents are composed, for example, of alkylalkoxysilanes (in particular alkyltriethoxysilanes), polyols, polyethers (for example polyethylene glycols), primary, secondary or tertiary amines (for example trialkanolamines) and α,ω-dihydroxylated polydimethylsiloxanes. Such a processing aid, when one of them is used, is employed in a proportion of 1 to 10 parts by weight and preferably of 2 to 8 parts by weight, per 100 parts of reinforcing white filler.

Fifth Subject Matter of the Invention

The process for the preparation of the diene elastomer compositions comprising a reinforcing white filler and at least one coupling agent can be carried out according to a conventional one-or two-stage procedure.

According to the one-stage process, all the necessary constituents, with the exception of the vulcanization agent(s) and optionally of the vulcanization accelerator(s) and/or of the vulcanization activator(s), are introduced into and kneaded in a conventional internal mixer, for example of Banbury type or Brabender type. The result of this first mixing stage is subsequently taken up on an external mixer, generally an open mill, and the vulcanization agent(s) and optionally the vulcanization accelerator(s) and/or the vulcanization activator(s) is (are) then added thereto.

It may be advantageous, for the preparation of certain articles, to employ a two-stage process in which both stages are carried out in an internal mixer. In the first stage, either all the necessary constituents, with the exception of the vulcanization agent(s) and optionally of the vulcanization accelerator(s) and/or of the vulcanization activator(s), are introduced and kneaded or a portion of the necessary constituents, the same exclusion rule being applied, are introduced and kneaded. The aim of the second stage which follows is essentially to subject the blend from the first stage, optionally completed by the addition of the missing necessary constituent(s), with application of the same exclusion rule, to an additional heat treatment. The result of this second stage is also subsequently taken up on an external mixer in order to add thereto the vulcanization agent(s) and optionally the vulcanization accelerator(s) and/or the vulcanization activator(s). The working phase in an internal mixer is generally carried out at a temperature ranging from 80 to 200° C., preferably from 80 to 180° C. This first working phase is followed by the second working phase in an external mixer, the operation being carried out at a lower temperature, generally of less than 120° C. and preferably ranging from 20 to 80° C.

The final composition obtained is subsequently calendered, for example in the form of a sheet or also of a profiled element which can be used for the manufacture of articles made of elastomer(s).

The vulcanization (or curing) is carried out in a known way at a temperature generally ranging from 130 to 200° C., optionally under pressure, for a sufficient time which can vary, for example, between 5 and 90 minutes depending in particular on the curing temperature, the vulcanization system adopted and the vulcanization kinetics of the composition under consideration.

It is obvious that the present invention, taken in its fourth subject matter, relates to the elastomer compositions described above both in the uncured state (that is to say, before curing) and in the cured state (that is to say, after crosslinking or vulcanization).

Sixth Subject Matter of the Invention

The elastomer compositions according to the invention can be used to prepare finished or semifinished articles made of elastomer(s) having a body comprising said compositions. These compositions are, for example, of use in the preparation of articles consisting of footwear soles, tires (in particular tire treads), conveyor belts, power transmission belting, flexible pipes, expansion joints, seals for domestic electrical appliances, engine supports, cables, cable sheaths or cableway rollers.

The following examples illustrate the present invention without limiting the scope thereof.

EXAMPLES

The $^{29}$Si NMR, $^1$H NMR and $^{13}$C NMR analyses are carried out under the following conditions.

$^{29}$Si NMR

Equipment:

The one-dimensional silicon-29 NMR analyses are carried out with a Bruker AMX 300 spectrometer and a 10 mm selective $^{29}$Si probe operating with an observation frequency for the silicon at 59 MHz.

The chemical shifts (δ) are expressed in ppm; tetramethylsilane is used as external reference for the $^1$H and $^{29}$Si chemical shifts. The temperature is controlled by a variable temperature unit (±0.1° K.). The NMR spectra are recorded at 300K.

Use is made, in order to obtain the proton-decoupled silicon-29 NMR spectra, of an accumulation sequence with proton decoupling of "inverse gated" type (WALTZ-16). The silicon-29 pulse angle is equal to 45° and the time between two silicon pulses is set at 4.5 seconds. The free precession signal (FID) is obtained after 4096 accumulations. The spectral width is 10 870 Hz and the number of points defining the free precession signal is equal to 32 768.

Preparation of Samples:

For the samples which require the recording of one-dimensional silicon NMR spectra, approximately 2 ml of silicon-comprising compounds are dissolved in 7 ml of a deuterated chloroform solution comprising $2.5 \times 10^{-2}$ mol/l of Fe(acac)$_3$ (acac=acetylacetonate).

$^1$H NMR and $^{13}$C NMR

Equipment:

Preparation of samples: 0.1 ml of sample in 0.5 ml of CDCl$_3$

Spectrometer: Bruker AMX 300

Probe: QNP 5 mm ($^1$H, $^{13}$C, $^{31}$P, $^{19}$F)

The NMR spectra are recorded at 300K (±0.1K).

$^1$H NMR Analysis:

Use is made of a simple acquisition sequence, with a pulse angle of 30°, a time between pulses of 4.6 seconds and 256 accumulations. The spectral width is 4500 Hz and no mathematical processing is carried out. The observation frequency is 300 MHz.

$^{13}$C NMR analysis:

Use is made of an accumulation sequence with proton decoupling (WALTZ-16), with a pulse angle of 30°, a time between pulses of 3 seconds and 8192 accumulations. The spectral width is 20 000 Hz and the signal is processed by an exponential function before the Fourier transform. The observation frequency is 75 MHz.

The deuterated solvent (CDCl$_3$) serves to compensate for possible drifts in the magnetic field and makes it possible to calibrate the spectra with regard to chemical shift.

Example 1 is a polysulfane synthesis.

Examples 2 to 9 are syntheses of bis(monoethoxydimethylsilane) polysulfide.

Example 10 is an illustration of the addition of a thiophosphorus compound to allyldimethylethoxysilane.

Example 11 is an addition of polysulfane to methallyldimethylethoxysilane.

Example 12 illustrates a β addition which makes it possible to obtain a bistrichlorosilane polysulfide.

Example 13 illustrates a β addition which makes it possible to obtain a bistriethoxysilane polysulfide.

Example 14 illustrates the route for addition of a polysulfane to the carbon in the γ position of the allyl Y radical of the starting allyldimethylethoxysilane (I).

Examples 15 and 16 illustrate the optional stage of hydrolysis of alkoxysilane polysulfides obtained in accordance with the process according to the invention.

Example 17 illustrates the coupling agent application in an elastomer composition.

Example 1

100.20 g of Na$_2$S$_4$ (575.2 mmol) and 151 g of water are introduced into a 1 liter reactor. 500 ml of 37% HCl are subsequently added. The temperature is subsequently maintained at approximately −20 to −15° C. for 1 hour after the HCl has finished being run in. The mixture is subsequently allowed to return to ambient temperature. 39 g of a yellow oil are recovered by separation by settling, the analyses of which indicate a structure of HSxH type with a molar distribution of x=1/2/3/4/5/6 of 4/2/26/12/29/27(%). This structure is also confirmed by Raman analysis.

Addition in the beta position (examples 2-13)

Example 2

1.00 g (6.94 mmol) of allyldimethylethoxysilane, 1 ml of toluene and 0.459 g (3.53 mmol) of the polysulfane prepared in example 1 are introduced under argon into a 10 ml polyethylene reactor. Reaction is allowed to take place at 25° C. for 16 hours.

Cooling is carried out and then the sulfur formed is filtered off and the toluene is evaporated. The reactants are completely converted. The derivative below, exhibiting a mean number x of 4-5, is obtained with a virtually quantitative yield. The $^1$H NMR and Raman analyses confirm the molecular structure. The yield is greater than 95%.

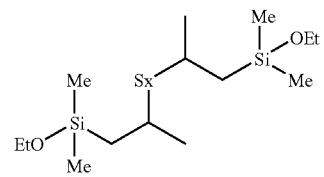

Example 3

1.08 g (7.54 mmol) of allyldimethylethoxysilane and 0.90 g (6.98 mmol) of the polysulfane prepared in example 1 are introduced under argon into a 40 ml stainless steel autoclave. The reactor is brought to 120° C. for 16 hours.

Cooling is allowed to take place. The sulfur formed is filtered off and 854 mg of a light yellow liquid are recovered, which liquid has a structure identical to that of the product obtained on conclusion of example 2.

Example 4

1.03 g (7.21 mmol) of allyldimethylethoxysilane and 0.80 g (6.21 mmol) of the polysulfane prepared in example 1 are introduced under argon into a 40 ml stainless steel autoclave. The reactor is brought to 100° C. for 16 hours.

Cooling is allowed to take place. The sulfur formed is filtered off and 538 mg of a light yellow liquid are recovered, which liquid has a structure identical to that of the product obtained on conclusion of example 2.

Example 5

1.04 g (7.26 mmol) of allyldimethylethoxysilane and 0.90 g (6.98 mmol) of the polysulfane prepared in example 1 are introduced under argon into a 40 ml stainless steel autoclave. The reactor is brought to 100° C. for 16 hours.

Cooling is allowed to take place. The sulfur formed is filtered off and 683 mg of a light yellow liquid are recovered, which liquid has a structure identical to that of the product obtained on conclusion of example 2.

Example 6

1.09 g (7.59 mmol) of allyldimethylethoxysilane and 0.91 g (7.01 mmol) of the polysulfane prepared in example 1 are introduced under argon into a 40 ml stainless steel autoclave. The reactor is brought to 100° C. for 16 hours.

Cooling is allowed to take place. The sulfur formed is filtered off and 734 mg of a light yellow liquid are recovered, which liquid has a structure identical to that of the product obtained on conclusion of example 2.

Example 7

1.01 g (7.07 mmol) of allyldimethylethoxysilane and 1.04 g (7.99 mmol) of the polysulfane prepared in example 1 are introduced under argon into a polyethylene reactor.

The reactor is irradiated with a lamp (HP—Hg) for 150 minutes.

The sulfur formed is filtered off and 743 mg of a light yellow liquid are recovered, which liquid has a structure identical to that of the product obtained on conclusion of example 2.

Example 8

20 g (0.134 mol) of allyldimethylethoxysilane and 19.6 g (0.137 mol) of the polysulfane prepared in example 1 are introduced under argon into a 40 ml stainless steel autoclave. The reactor is brought to 150° C. for 16 hours.

Cooling is allowed to take place. The sulfur formed is filtered off and 27.5 g of a light yellow liquid are recovered, which liquid has a structure identical to that of the product obtained on conclusion of example 2. The yield is 95%.

Example 9

20.01 g of allyldimethylethoxysilane (129.2 mmol, 1 eq.) and 18.16 g of the polysulfane prepared in example 1 (132.2 mmol, 1.02 eq.) are introduced into a 40 ml hastelloy autoclave under autogeneous pressure with an oil bath and magnetic stirring. The two reactants are immiscible. The reactor is closed, then placed under stirring and heated at 150° C. for 16 hours. Cooling is allowed to take place and 25.65 g of a yellow oil are obtained, the analyses of which confirm the single structure below. The isolated yield is approximately 90% and the purity is greater than 98%.

The bis(monoethoxydimethylsilane) polysulfide product obtained in examples 2 to 9 exhibits the following formula:

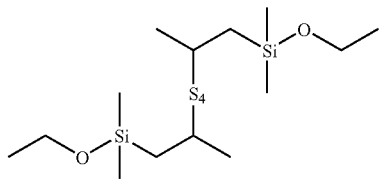

This single structure is confirmed by the following NMR analyses:

$^1$H NMR Analysis

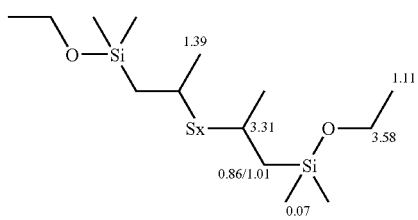

$^{13}$C NMR Analysis

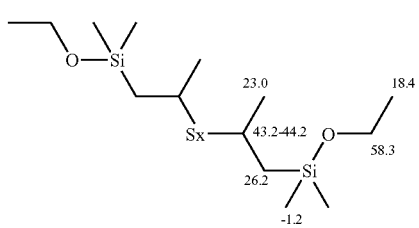

$^{29}$Si NMR Analysis

| δ ppm | Nature | Units |
|---|---|---|
| 13.7 | Singlet | $M_{OR}$ |

| Distribution of the sulfur-comprising units (study on $^{13}$C NMR spectrum) | | | | | |
|---|---|---|---|---|---|
| | Distribution of the intramolecular sulfurs | | | | |
| | $S_1$ | $S_2$ | $S_3$ | $S_{4-5}$ | $S_{\geq 6}$ |
| δ (ppm) | 34.52/34.84 | 43.14/43.23 | 43.61/43.66 | 43.99/44.05 | >44.13 |
| Molar % (standardization at 100) | 4.9 | 10.5 | 25.9 | 26.6 | 32.1 |

Example 10

1.681 g of allyldimethylethoxysilane (11.67 mmol, 1 eq.) and 2.40 g of O,O'-diethyl dithiophosphate (11.70 mmol, 1 eq.) are introduced into a dry 25 ml three-necked flask under argon with magnetic stirring, a temperature probe, an oil bath and a reflux condenser. The translucent mixture, which is slightly yellow in color, is heated at 60° C. for 3 hours. 3.65 g of an oil are obtained, the NMR and IR analyses of which confirm the sole formation of the derivative below. The isolated yield is approximately 90%. The purity is greater than 98%.

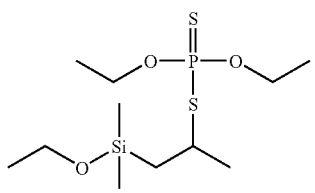

Example 11

3.01 g of methallyldimethylethoxysilane (17.53 mmol, 1 eq.) and 2.37 g of the polysulfane prepared in example 1 (18.23 mmol, 1.04 eq.) are introduced into a 40 ml hastelloy autoclave under autogeneous pressure with a magnetic stirrer and an oil bath. The two products are immiscible. Heating is carried out at 150° C. with stirring for 20 hours.

Cooling is allowed to take place to ambient temperature. On opening the reactor, a mobile orange-colored liquid which wets sulfur grains is found to be present. Filtration is carried out and a weight w of 3.038 g is obtained (yield: 78%). The NMR analysis shows that the product formed has the following structure with a molar purity of greater than 97%:

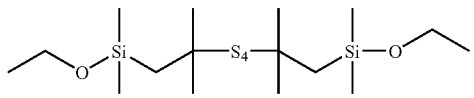

Example 12

Synthesis of $Cl_3Si$—$CH_2$—$CH$—$(CH_3)$—$S_x$—$(CH_3)$—$CH$—$CH_2$—$SiCl_3$

The following are introduced into a 40 ml hastelloy reactor under autogeneous pressure with a magnetic stirrer and an oil bath and under an argon atmosphere:
1.0 g of trichloroallylsilane (5.41 mmol) and
0.78 g of polysulfane (5.41 mmol) of general formula $HS_yH$ (with a mean y number of 5-6).

The two liquids are immiscible. The reactor is closed and is brought to 110° C. for 21 hours.

Cooling is allowed to take place and then the reactor is opened. The latter comprises a liquid mixed with sulfur. Filtration is carried out and a yellow oil is obtained.

The $^1H$ and $^{13}C$ NMR analyses confirm the structure of the following product formed, with an isolated molar yield of 86%:
$Cl_3Si$—$CH_2$—$CH$—$(CH_3)$—$S_x$—$(CH_3)$—$CH$—$CH_2$—$SiCl_3$, with a mean x number of 3-5.

Example 13

Synthesis of $(C_2H_5O)_3Si$—$CH_2$—$CH$—$(CH_3)$—$S_x$—$(CH_3)$—$CH$—$CH_2$—$Si(OC_2H_5)_3$ The following are introduced into a 40 ml hastelloy reactor under autogeneous pressure with a magnetic stirrer and an oil bath and under an argon atmosphere:
1.36 g of triethoxyallylsilane (6.47 mmol) and
0.853 g of polysulfane (6.85 mmol) of general formula $HS_yH$ (with a mean y number of 5-6).

The two liquids are immiscible. The reactor is closed and brought to 150° C. for 16 hours.

Cooling is allowed to take place and then the reactor is opened. The latter comprises a liquid mixed with sulfur. Filtration is carried out and a yellow oil is obtained (945 mg).

The $^1H$ and $^{13}C$ NMR analyses confirm the structure of the following product formed, with an isolated molar yield of 64%:
$(EtO)_3Si$—$CH_2$—$CH$—$(CH_3)$—$S_x$—$(CH_3)$—$CH$—$CH_2$—$Si(OEt)_3$, with a mean x number of 3-5.

Addition in the gamma position (example 14).

Example 14

1.50 g of dimethylethoxyisoprenylsilane (8.72 mmol, 1 eq.) and 1.16 g of the polysulfane prepared in example 1 (8.92 mmol, 1.02 eq.) are introduced into a 40 ml hastelloy autoclave under autogeneous pressure with a magnetic stirrer and an oil bath. The two products are immiscible. Heating is carried out at 150° C. with stirring for 20 hours.

Cooling is allowed to take place to ambient temperature. On opening the reactor, a brown oil with a weight w of 1.68 g (with a yield equal to 81%) is found to be present, the NMR analysis of which confirms the presence of the following sole product:

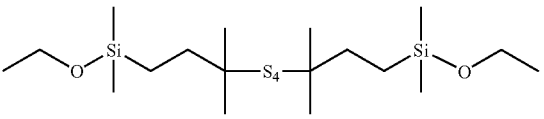

Example 15

Hydrolysis, in a water-acetonitrile mixture, by acid catalysis, of the bis(monoethoxydimethylsilane) polysulfide obtained in example 9

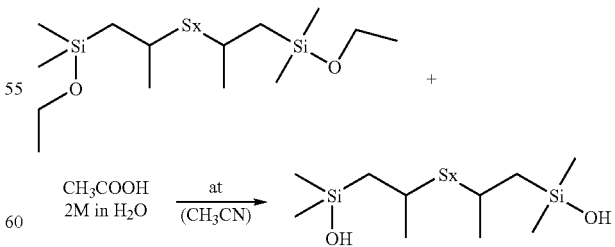

2 g (0.0046 mol, 1 molar equivalent) of the bis(monoethoxydimethylsilane) polysulfide obtained in example 9 and then 20 ml of $CH_3CN$ (immiscible oily phase) are charged to a 100 ml single-necked flask. 14 ml (0.028 mol, 6 equivalents) of 2M aqueous acetic acid (immiscible with the preceding mixture) are subsequently rapidly introduced at ambient temperature. Stirring is carried out at ambient temperature for 30 minutes. The reaction mass is extracted with 40 ml of diethyl ether. The organic phase is dried over MgSO$_4$, filtered under vacuum and then evaporated to dryness on a rotary evaporator. A yellow oil is obtained with a yield of approximately 90%, the NMR analyses of which show the following molar composition:

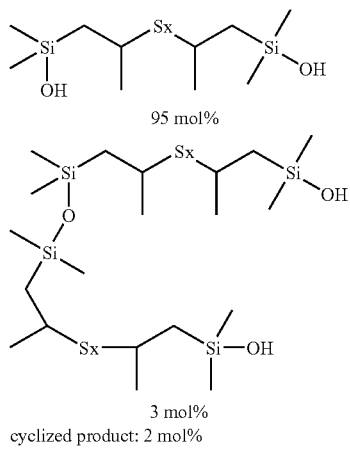

cyclized product: 2 mol%

Example 16

Hydrolysis in pure water of the bis(monoethoxydimethylsilane) polysulfide obtained in example 9

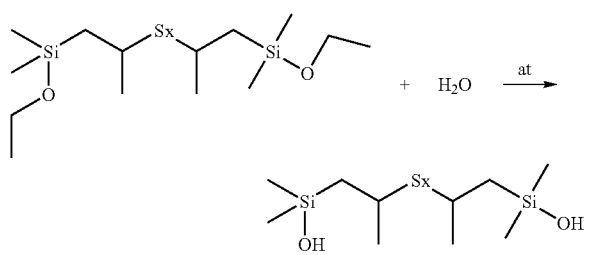

1 g (0.0023 mol, 1 molar equivalent) of the bis(monoethoxydimethylsilane) polysulfide obtained in example 9 and then 25 ml of H$_2$O (immiscible) are charged to a 100 ml single-necked flask.

The reaction mass is stirred at ambient temperature for 24 hours. The final mass is subsequently extracted with 60 ml of diethyl ether. The organic phase is dried over MgSO$_4$, filtered under vacuum and then evaporated to dryness on a rotary evaporator. A yellow oil is obtained with a yield of greater than 95%, the NMR analyses of which show the following molar composition:

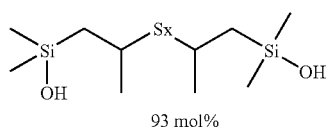

93 mol%

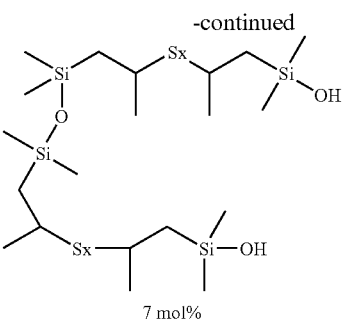

7 mol%

Example 17

35 g of Mg turnings (1.53 eq.), 198.5 g of anhydrous dibutyl ether and 70 mg of iodine are introduced into a jacketed 1 liter reactor which has been rendered inert with nitrogen and which has a temperature probe and a mechanical stirrer. The Mg is left to activate at 130° C. Once the reaction mass has decolorized, 140 g of diethoxydimethylsilane are introduced, still at 130° C. 88 g of allyl chloride (1.22 eq.), diluted in 212 g of anhydrous dibutyl ether, are then run in gently (time of approximately 5.5 hours). The reaction medium is maintained at 130° C. for 16 hours; a degree of conversion of greater than 95% is obtained. The reaction mass is subsequently distilled under reduced pressure (minimum pressure: 350 mbar) using a 60 cm packed column, with return and a reflux ratio of 1/10. After distillation, the isolated yield of alllyldimethylethoxysilane is 79%, without formation of bisallyldimethylsilane.

Example 18

500 ml of 37% HCl and 151 g of water are introduced into a 1 liter reactor. 100.20 g of Na$_2$S$_4$ (575.2 mmol) are subsequently added while maintaining the bulk temperature at 0° C. The temperature is subsequently maintained at approximately 0° C. for 1 hour after the Na$_2$S$_4$ has finished being run in. The mixture is subsequently allowed to return to ambient temperature. 39 g of a yellow oil are recovered by separation by settling (lower phase), the analyses of which indicate a structure of HSxH type with a molar distribution of x=1/2/3/4/5/6 of 4/2/26/12/29/27(%) (determination by $^1$H NMR). This structure is also confirmed by Raman analysis.

Example 19

Addition in the Beta Position

The allyldimethylethoxysilane (22.5 g) prepared in example 17 is introduced into a 100 ml reactor which has been rendered inert. The temperature of the reaction medium is brought to 60° C. and then the polysulfane prepared in example 18 (23.8 g) is slowly added (the bulk temperature must not exceed 80° C.) with stirring. The reaction medium is kept stirred for 20 hours at a temperature of 20° C. At the end of the reaction, the solid is filtered off. The filtrate is diluted with n-heptane (48 g). The organic phase is then washed 3 times with a buffer solution (Na$_2$CO$_3$/NaHCO$_3$). The solvent is removed from the organic phase by evaporation under partial vacuum. Finally, the final product is filtered in order to remove insoluble materials. The derivative below is obtained (62 g), which derivative exhibits a mean x number of 4-5. The $^1$H NMR and Raman analyses confirm the molecular structure.

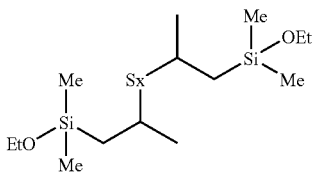

Example 20

This example illustrates the use and the behavior of an alkoxysilane polysulfide according to the invention, in this case bis(monoethoxydimethylsilane) polysulfide obtained in example 9 (or bis(monoethoxydimethylsilylisopropyl) etra-sulfide (MESiPrT)), as coupling agent in an industrial rubber composition comprising silica as reinforcing filler.

1. Make-up of the Elastomeric Compositions

The following compositions, the make-up of which is shown in table 1 below (the contents of the constituents are expressed in parts by weight), are prepared in an internal mixer of Brabender type.

TABLE 1

| Composition | Reference (R) | Invention (I) |
|---|---|---|
| SBR rubber[1] | 137.5 | 137.5 |
| Silica[2] | 80 | 80 |
| Silane, TESPT[3] | 6.4 | |
| Silane, MESiPrT[4] | | 4.7 |
| ZnO[5] | 2.5 | 2.5 |
| Stearic acid | 2 | 2 |
| 6-PPD[6] | 1.9 | 1.9 |
| DPG[7] | 1.5 | 1.1 |
| CBS[8] | 2 | 2 |
| TBzTD[9] | 0.2 | 0.2 |
| Sulfur[10] | 1.1 | 1.1 |

[1]Styrene-butadiene copolymer in solution of Buna VSL5025-1 type, sold by Lanxess (with 50% (±4%) of vinyl units, 25% (±2%) of styrene units, Tg of approximately −20° C., extended with 37.5% (±2.8%) by weight of oil per 100 parts of SBR)
[2]Precipitated silica Z1165MP, sold by Rhodia
[3]Silica/rubber coupling agent formed of bis(triethoxysilylpropyl) tetrasulfide of formula $(C_2H_5O)_3Si-(CH_2)_3-S_4-(CH_2)_3-Si(OC_2H_5)_3$, sold by Dow Corning under the name Z-6940
[4]Coupling agent prepared in example 9, in accordance with the invention
[5]Vulcanization activator
[6]N-1,3-Dimethylbutyl-N-phenyl-para-phenylenediamine (Santoflex 6-PPD, sold by Flexsys)
[7]Diphenylguanidine (Vulkacit D, sold by Bayer)
[8]N-Cyclohexyl-2-benzothiazolesulfenamide (Rhenogran CBS-80, sold by Lanxess)
[9]Tetrabenzylthiuram disulfide (Perkacit TBzTD, sold by Flexsys)
[10]Vulcanization agent 2. Preparation of the Compositions The process of the preparation of each rubber composition is carried out in two successive phases.

A first "nonproductive" phase makes it possible a high temperature thermomechanical working (up to a maximum temperature of between 130 and 160° C.). It is followed by a second "productive" phase of mechanical working at temperatures of less than 110° C., this phase making possible the introduction of the vulcanization system.

The first phase is carried out using a mixing device, in this case an internal mixer of Brabender brand (capacity of 70 ml). The filling coefficient is 0.75. The starting temperature and the speed of the rotors are set on each occasion so as to achieve dropping temperatures for the mixture in the vicinity of 130-160° C. It is broken down here into two passes.

It makes it possible to incorporate, in a first pass, the elastomer and then the reinforcing filler composed of the silica (fractional introduction) with the coupling agent and the stearic acid. For this pass, the duration is between 2 and 10 minutes.

After cooling the blend (temperature of less than 100° C.), a second pass makes it possible to incorporate the zinc oxide and the antioxidant 6-PPD. For this pass, the duration is between 2 and 5 minutes.

After cooling the blend (temperature of less than 100° C.), the second phase makes possible the introduction of the vulcanization system (sulfur, DPG, CBS and TBzTD). It is carried out on an open mill preheated to 50° C. The duration of this phase is between 5 and 10 minutes.

After homogenization, the final compositions are subsequently calendered in the form of sheets with a thickness of 2 to 3 mm.

The rheological properties are measured on these compositions in the uncured state, which makes it possible in particular to optimize the vulcanization time and temperature.

The mechanical and dynamic properties of the optimally vulcanized compositions are subsequently measured.

3. Rheological Properties

The measurements are carried out on the compositions in the uncured state.

The results relating to the rheology test carried out at 160° C. using a Monsanto 100 S ODR rheometer according to the standard DIN 53529 are given in table 2 below.

According to this test, the test composition is placed in the test chamber adjusted to a temperature of 160° C. for 30 minutes and the resistive torque opposed by the composition to a low-amplitude oscillation (3°) of a biconical rotor included in the test chamber is measured, the composition completely filling said chamber.

The following are determined from the curve of variation of the torque as a function of time:

the minimum torque (Tm), which reflects the viscosity of the composition at the temperature under consideration,
the maximum torque (TM),
the delta-torque ($\Delta T = TM - Tm$), which reflects the degree of crosslinking caused by the action of the crosslinking system and, if necessary, of the coupling agent,
the time T90 necessary in order to obtain a state of vulcanization corresponding to 90% of the complete vulcanization (this time is taken as vulcanization optimum),
the scorch time Ts2, which corresponds to the time necessary in order to have a rise of 2 points above the minimum torque at the temperature under consideration (160° C.) and which reflects the time during which it is possible to process the uncured blends at this temperature without having initiation of the vulcanization.

TABLE 2

| | Composition R | Composition I |
|---|---|---|
| Tm (dN · m) | 17.3 | 17.3 |
| TM (dN · m) | 64.1 | 68.9 |
| ΔT (dN · m) | 46.9 | 51.6 |
| Ts2 (min) | 5.75 | 4.72 |
| T90 (min) | 17.2 | 13.68 |
| Rcross_max (dN · m/min)* | 5.08 | 9.51 |

*maximum crosslinking rate (derivative of the curve of torque as a function of time)

It is found that the coupling agent according to the present invention makes it possible to improve the vulcanization kinetics (Vcross_max or T90-Ts2) of the corresponding composition with respect to the reference composition, without damaging the viscosity of the uncured blend (the minimum torque is identical).

The use of the coupling agent according to the invention, without damaging the processing, makes possible a saving in the final curing time.

4. Mechanical Properties of the Vulcanized Compositions

The measurements are carried out on the optimally vulcanized compositions ($t_{98}$) for a temperature of 160° C.

Uniaxial tensile tests are carried out in accordance with the instructions of the standard NF T 46-002 with test specimens of H2 type at a rate of 500 mm/min on an Instron 5564 device.

The x % moduli correspond to the stress measured at x % of tensile strain.

It is possible to determine a breaking energy, which represents the area under the curve, expressed in joules.

The measurement of Shore A hardness of the vulcanisates is carried out according to the instructions of the standard ASTM D 2240. The value given (in points) is measured at 15 seconds.

The properties measured are collated in table 3 below.

TABLE 3

|   | Composition R | Composition I |
| --- | --- | --- |
| 10% Modulus (MPa) | 0.59 | 0.57 |
| 100% Modulus (MPa) | 2.57 | 2.83 |
| 300% Modulus (MPa) | 13.1 | 12.5 |
| Tensile strength (MPa) | 19.9 | 20.3 |
| Elongation at break (%) | 406.2 | 455.0 |
| Breaking energy (J) | 2.79 | 3.55 |
| Shore A hardness (pts) | 64 | 63 |

Composition I, which comprises a coupling agent according to the present invention, exhibits a good compromise in mechanical properties without deterioration in the final properties and with a very satisfactory hardness.

5. Dynamic Properties of the Vulcanized Compositions

The measurements are carried out on the optimally vulcanized compositions ($t_{98}$) for a temperature of 160° C.

The dynamic properties are measured on a Metravib VA3000 viscosity analyzer according to the standard ASTM D 5992.

5.1—The values for loss factor (tan δ) and compressive dynamic complex modulus (E*) are recorded on vulcanized samples provided in the form of cylindrical test specimens having a cross section of 95 mm² and a height of 14 mm. Each sample is subjected at the start to a 10% prestrain and then to a sinusoidal strain in alternating compression of ±2%. The measurements are carried out at 60° C. and at a frequency of 10 Hz.

The results are shown in table 4.

TABLE 4

|   | Composition R | Composition I |
| --- | --- | --- |
| E* (60° C., 10 Hz) | 8.20 | 6.63 |
| tan δ (60° C., 10 Hz) | 0.140 | 0.142 |

5.2—The values for loss factor (tan δ) and for amplitude of the dynamic shear elastic modulus (ΔG') are recorded on vulcanized samples provided in the form of parallelepipedal test specimens having a cross section of 8 mm² and a height of 7 mm. Each sample is subjected to a double alternating sinusoidal shear strain at a temperature of 40° C. and at a frequency of 10 Hz. The strain amplitude sweeping process is carried out according to an outward-return cycle, from 0.1% to 50% and then returning from 50% to 0.1%.

The results, presented in table 5 below, result from the return strain amplitude sweep and relate to the maximum value of the loss factor (tan δ max return) and to the amplitude of the elastic modulus (ΔG') between the values at 0.1% and at 50% strain (Payne effect)

TABLE 5

|   | Composition R | Composition I |
| --- | --- | --- |
| tan δ max return (40° C., 10 Hz) | 0.274 | 0.261 |
| ΔG' (40° C., 10 Hz) | 3.36 | 2.95 |

Composition I, which comprises a coupling agent according to the invention, exhibits a highly satisfactory compromise in dynamic properties.

This is because it is found that, at 40° C. and 60° C., the value of the loss factor (tan δ), which reflects the energy absorbed or restored by the vulcanisate when subjected to a strain under the test conditions mentioned, of composition I comprising a coupling agent according to the invention is similar to that of reference composition R, independently of the mode of dynamic stresses.

A reduction in the nonlinearity at 40° C., associated with the Payne effect, is also found for composition I comprising a coupling agent according to the invention. Composition I consequently exhibits hysteresis properties which are not deteriorated with respect to reference composition R.

The invention claimed is:

1. A process for the preparation of at least one alkoxy-and/or halosilane (poly)sulfide, comprising reacting, via an ionic addition mechanism, at least one sulfur-containing reactant (Rs) with at least one alkoxy-and/or halosilane of formula (I):

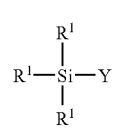

(I)

in which:
the $R^1$ symbols, which may be identical or different, are each:
a linear, branched or cyclic alkyl radical having from 1 to 20 carbon atoms,
an aryl radical having from 6 to 18 carbon atoms,
an —$OR^2$ alkoxy radical, wherein $R^2$ is a linear, branched or cyclic alkyl radical having from 1 to 20 carbon atoms or an aryl radical having from 6 to 18 carbon atoms,
an arylalkyl radical or an alkylaryl radical ($C_6$-$C_{18}$ aryl, $C_1$-$C_{20}$ alkyl),
a hydroxyl radical,
or a halogen,
with the proviso that at least one of these $R^1$ radicals is —$OR^2$, —OH or a halogen and such $R^1$ radicals, when they are neither hydroxyl nor halogens, optionally bear at least one halogenated substituent;
the Y symbol has the formula (II):

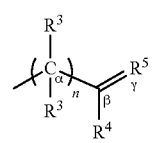

(II)

in which:
the $R^3$ and $R^4$ symbols, which may be identical or different, are each hydrogen or a monovalent hydrocarbon radical selected from the group consisting of a linear, branched or cyclic alkyl radical having from 1 to 20 carbon atoms and a linear, branched or cyclic alkoxyalkyl radical having from 1 to 20 carbon atoms;

the $R^5$ symbol is $CH_2$ or $CR^6R^7$, wherein $R^6$ and $R^7$, which may be identical or different, are each hydrogen or a monovalent hydrocarbon radical selected from the group consisting of a linear, branched or cyclic alkyl radical having from 1 to 20 carbon atoms and a linear, branched or cyclic alkoxyalkyl radical having from 1 to 20 carbon atoms; and the n symbol is an integer greater than or equal to 1.

2. The process as defined by claim 1, wherein at least one of the $R^1$ radicals is $-OR^2$.

3. The process as defined by claim 1, wherein Y has the following formula (II.1):

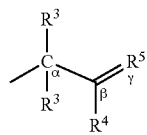

in which:
the $R^3$ and $R^4$ symbols, which may be identical or different, are each hydrogen or a monovalent hydrocarbon radical selected from the group consisting of a linear, branched or cyclic alkyl radical having from 1 to 20 carbon atoms and a linear, branched or cyclic alkoxyalkyl radical having from 1 to 20 carbon atoms;

the $R^5$ symbol is $CH_2$ or $CR^6R^7$, wherein the $R^6$ and $R^7$ symbols, which may be identical or different, are each hydrogen or a monovalent hydrocarbon radical selected from the group consisting of a linear, branched or cyclic alkyl radical having from 1 to 20 carbon atoms and a linear, branched or cyclic alkoxyalkyl radical having from 1 to 20 carbon atoms.

4. The process as defined by claim 1, wherein $R^4$ is H and $R^5$ is $CH_2$ and the ionic addition of (Rs) takes place on the β carbon of the alkoxy-and/or halosilane (I).

5. The process as defined by claim 1, wherein $R^4$ is an alkyl radical, and $R^5$ is $CH_2$ and the ionic addition of (Rs) takes place on the β carbon of the alkoxy-and/or halosilane (I).

6. The process as defined by claim 1, wherein $R^4$ is H and $R^5$ is $CR^6R^7$, in which $R^6$ and $R^7$ are each $-CH_3$, and the ionic addition of (Rs) takes place on the γ carbon of the alkoxy-and/or halosilane (I).

7. The process as defined by claim 1, wherein (Rs) is selected from the group consisting of $HS_xH$, O,O'-dialkyl dithiophosphate (HSPS), $M'_2S_x$, in which M' is an alkali metal, xS, $H-S_x$ and mixtures thereof, and the x symbol is an integer or fractional number ranging from 1 to 10.

8. The process as defined by claim 1, wherein (Rs) is O,O'-dialkyl dithiophosphate (HSPS) or HSH and the product of the reaction from (I) and (Rs) is reacted with a secondary sulfur-comprising reactant (Rs2) selected from the group consisting of $S_x$ and/or X1S—SX2, in which X1 and X2 are a halogen and the x symbol is an integer or fractional number ranging from 1 to 10, this secondary sulfurization optionally being carried out in a basic medium.

9. The process as defined by claim 1, wherein the (I)/(Rs) molar ratio ranges from 5 to 0.1.

10. The process as defined by claim 1, wherein the ionic addition is carried out under an inert atmosphere and/or in the presence of solvent(s) selected from the group consisting of unreactive hydrocarbon solvents and aromatic hydrocarbons devoid of carbonyl or hydroxyl functional groups.

11. The process as defined by claim 1, comprising at least one hydrolysis stage to convert at least one of the $R^1$ radicals corresponding to $-OR^2$ of the alkoxy-and/or halosilane (poly)sulfide to a hydroxyl group.

\* \* \* \* \*